United States Patent
Strothers et al.

(10) Patent No.: US 8,030,082 B2
(45) Date of Patent: Oct. 4, 2011

(54) LIQUID-PARTICLE ANALYSIS OF METAL MATERIALS

(75) Inventors: Susan D. Strothers, Spokane, WA (US); Janine K. Kardokus, Veradale, WA (US); Brett M. Clark, Spokane, WA (US)

(73) Assignee: Honeywell International Inc., Morristown, NJ (US)

( * ) Notice: Subject to any disclaimer, the term of this patent is extended or adjusted under 35 U.S.C. 154(b) by 1025 days.

(21) Appl. No.: 11/331,489

(22) Filed: Jan. 13, 2006

(65) Prior Publication Data

US 2007/0166828 A1    Jul. 19, 2007

(51) Int. Cl.
*G01N 33/20* (2006.01)
*G01N 33/53* (2006.01)

(52) U.S. Cl. ........... 436/73; 436/75; 356/336; 356/337; 356/338; 356/341; 250/574

(58) Field of Classification Search .................... 436/73, 436/75; 356/336, 337, 338, 341; 250/574
See application file for complete search history.

(56) References Cited

U.S. PATENT DOCUMENTS

| | | | |
|---|---|---|---|
| 4,616,691 A | 10/1986 | Voss | |
| 4,623,014 A | 11/1986 | Faessler et al. | |
| 4,641,703 A | 2/1987 | Voss et al. | |
| 4,668,288 A | 5/1987 | Ouchi et al. | |
| 4,699,656 A | 10/1987 | Mantymaki | |
| 4,714,104 A | 12/1987 | Ouchi et al. | |
| 4,724,896 A | 2/1988 | Rose et al. | |
| 4,769,066 A | 9/1988 | Eidem | |
| 4,782,886 A | 11/1988 | Uchida et al. | |
| 4,790,874 A | 12/1988 | Lirones | |
| 4,794,086 A * | 12/1988 | Kasper et al. | 436/36 |
| 4,795,490 A | 1/1989 | Leckie et al. | |
| 4,830,667 A | 5/1989 | Marcuson et al. | |
| 5,042,561 A | 8/1991 | Chandley | |
| 5,071,471 A | 12/1991 | Miki et al. | |
| 5,106,411 A | 4/1992 | Miki et al. | |
| 5,211,216 A | 5/1993 | Drury et al. | |
| 5,215,571 A | 6/1993 | Marcuson et al. | |

(Continued)

FOREIGN PATENT DOCUMENTS

CN    1138124 C    2/2004

(Continued)

OTHER PUBLICATIONS

English Translation of 3rd Party Observation from Japanese Patent Office.

*Primary Examiner* — Krishnan S Menon
*Assistant Examiner* — Rebecca Fritchman

(57) ABSTRACT

The invention includes a method of detecting impurities in a metal-containing article. A portion of metal material is removed from a metal article and is solubilized in an acid or base-comprising liquid to produce a liquid sample. The liquid sample is subjected to an incident laser beam and light scattered from the sample is detected. The invention includes a method of analyzing a physical vapor deposition target material. A portion of target material is removed from the target and is rinsed with an acid-comprising solution. The portion of target material is dissolved to produce a liquid sample. The sample is subjected to an incident laser beam and scatter of the laser beam is detected to determine the number of particles present in the sample within a particular size range.

20 Claims, 3 Drawing Sheets

U.S. PATENT DOCUMENTS

| | | |
|---|---|---|
| 5,228,498 A | 7/1993 | Harada et al. |
| 5,263,531 A | 11/1993 | Drury et al. |
| 5,273,102 A | 12/1993 | Lillquist et al. |
| 5,291,940 A | 3/1994 | Borofka et al. |
| 5,404,928 A | 4/1995 | Ota et al. |
| 5,427,170 A | 6/1995 | Arakawa et al. |
| 5,454,416 A | 10/1995 | Ota et al. |
| 5,462,107 A | 10/1995 | Hasegawa et al. |
| 5,697,423 A | 12/1997 | Roder et al. |
| 5,706,880 A | 1/1998 | Ohnuma et al. |
| 5,733,500 A | 3/1998 | Meseha et al. |
| 5,738,163 A | 4/1998 | Demukai et al. |
| 5,839,500 A | 11/1998 | Roder et al. |
| 5,849,061 A | 12/1998 | Themelis et al. |
| 5,891,215 A | 4/1999 | Meseha et al. |
| 5,921,311 A | 7/1999 | Menendez et al. |
| 5,983,976 A | 11/1999 | Kono |
| 6,006,821 A | 12/1999 | Haun et al. |
| 6,019,159 A | 2/2000 | Roder et al. |
| 6,035,922 A | 3/2000 | Sugitani et al. |
| 6,089,308 A | 7/2000 | Roder et al. |
| 6,135,196 A | 10/2000 | Kono |
| 6,253,828 B1 | 7/2001 | Reiter |
| 6,276,434 B1 | 8/2001 | Kono |
| 6,283,197 B1 | 9/2001 | Kono |
| 6,287,364 B1 | 9/2001 | Mizuta et al. |
| 6,346,418 B1 * | 2/2002 | Chang et al. .............. 436/79 |
| 6,391,081 B1 | 5/2002 | Uchikoshi et al. |
| 6,403,043 B1 | 6/2002 | Utigard et al. |
| 6,446,703 B1 | 9/2002 | Roder et al. |
| 6,467,531 B1 | 10/2002 | Doney |
| 6,470,955 B1 | 10/2002 | Richard et al. |
| 6,474,399 B2 | 11/2002 | Kono |
| 6,540,006 B2 | 4/2003 | Kono |
| 6,640,879 B2 | 11/2003 | Richard et al. |
| 6,655,445 B2 | 12/2003 | Kono |
| 6,666,258 B1 | 12/2003 | Kono |
| 6,776,219 B1 | 8/2004 | Cornie et al. |
| 6,805,190 B2 | 10/2004 | Hamilton et al. |
| 6,837,299 B2 | 1/2005 | Schlienger et al. |
| 6,871,692 B2 | 3/2005 | Hamilton et al. |
| 6,942,006 B2 | 9/2005 | Kono |
| 7,073,558 B1 | 7/2006 | Nakajima |
| 7,311,847 B2 * | 12/2007 | Kashkoush ............... 210/739 |
| 2001/0045266 A1 | 11/2001 | Kono |
| 2003/0066620 A1 | 4/2003 | Kono |
| 2003/0201088 A1 | 10/2003 | Kono |
| 2004/0050525 A1 | 3/2004 | Kennedy et al. |
| 2004/0163669 A1 * | 8/2004 | Brueckner et al. .......... 134/1.2 |

FOREIGN PATENT DOCUMENTS

| | | |
|---|---|---|
| CN | 118/4337 C | 1/2005 |
| EP | 0293502 A1 | 12/1988 |
| EP | 0332490 B1 | 9/1989 |
| EP | 0416738 B1 | 9/1995 |
| EP | 0600324 B1 | 6/1999 |
| EP | 0717119 B1 | 4/2001 |
| EP | 1143234 A1 | 10/2001 |
| EP | 1143235 A1 | 10/2001 |
| EP | 1042087 B1 | 11/2001 |
| EP | 0992597 B1 | 7/2002 |
| EP | 0844966 B1 | 2/2003 |
| EP | 1415740 A1 | 5/2004 |
| EP | 1663547 A3 | 6/2006 |
| EP | 1573077 B1 | 8/2006 |
| JP | 55-134139 | 10/1980 |
| JP | 63-307226 | 12/1988 |
| JP | 64-017813 | 1/1989 |
| JP | 01-113658 | 5/1989 |
| JP | 3006336 A | 5/1989 |
| JP | 3032447 A | 6/1989 |
| JP | 04-099234 | 3/1992 |
| JP | 04-099235 | 3/1992 |
| JP | 04-099236 | 3/1992 |
| JP | 0412246 * | 9/1992 |
| JP | 2005-062958 A | 12/1993 |
| JP | 06-212302 | 8/1994 |
| JP | 06-299261 | 10/1994 |
| JP | 07-090409 | 4/1995 |
| JP | 11-092837 A | 4/1999 |
| JP | 2970234 B2 | 11/1999 |
| JP | 11316220 A | 11/1999 |
| JP | 2000-321193 A | 11/2000 |
| JP | 2000328152 A | 11/2000 |
| JP | 2001181750 A | 3/2001 |
| JP | 2001113347 A | 4/2001 |
| JP | 3203849 B2 | 8/2001 |
| JP | 2001-264232 A | 9/2001 |
| JP | 2001-349819 A | 12/2001 |
| JP | 2003129143 A | 8/2003 |
| JP | 2004066302 | 3/2004 |
| JP | 2004-212261 A | 7/2004 |
| JP | 2004256846 A | 9/2004 |
| JP | 2005-291993 A | 10/2005 |
| JP | 2006161082 A | 6/2006 |
| JP | 2006175505 A | 7/2006 |
| JP | 2006037163 A | 9/2006 |
| JP | 2003523831 A | 3/2007 |
| RU | 2087560 C1 | 8/1997 |
| WO | 92-15414 A1 | 9/1992 |
| WO | 01-36315 A1 | 5/2001 |
| WO | 02-22292 A1 | 3/2002 |
| WO | 03-038138 A1 | 5/2003 |
| WO | 2005-049874 A1 | 6/2005 |
| WO | 2006-103833 A1 | 10/2006 |

* cited by examiner

LIQUID-PARTICLE ANALYSIS OF METAL MATERIALS

TECHNICAL FIELD

The invention pertains to methods of detecting impurities in metal-containing articles and methods of analyzing physical vapor deposition target materials.

BACKGROUND OF THE INVENTION

High-purity metals and high-purity metal alloys are increasingly important in a wide range of technology areas. One area of extreme importance for high-purity metals is semiconductor fabrication. For semiconductor constructions, metallic purity can significantly affect semiconductor device quality and functionality. Accordingly, since impurities present in a source material can determine its suitability for use in semiconductor fabrication it is increasingly important to develop technology for detecting and/or quantifying impurities present in source materials.

Physical vapor deposition (PVD) methods are used extensively for forming thin metal films over a variety of substrates, including but not limited to, semiconductive substrates during semiconductor fabrication. A diagrammatic view of a portion of an exemplary PVD apparatus 10 is shown in FIG. 1. Apparatus 10 includes a target assembly 12. The target assembly illustrated includes a backing plate 14 interfacing a PVD or "sputtering" target 16. Alternative assembly configurations (not shown) have an integral backing plate and target.

Typically, apparatus 10 will include a substrate holder 18 for supporting a substrate during a deposition event. A substrate 20, such as a semiconductive material wafer is provided to be spaced from target 16. A surface 17 of target 16 can be referred to as a sputtering surface. In operation, sputtered material 18 is displaced from surface 17 of the target and deposits onto surfaces within the sputtering chamber including the substrate, resulting in formation of a layer or thin film 22.

Sputtering utilizing system 10 is most commonly achieved with a vacuum chamber by, for example, DC magnetron sputtering or radio frequency (RF) sputtering.

Various materials including metals and alloys can be deposited using physical vapor deposition. Common target materials include, for example, aluminum, titanium, copper, tantalum, nickel, molybdenum, gold, silver, platinum and alloys thereof. Sputtering targets are typically made of high-purity materials. However, even minute particles or inclusions such as, for example, oxides or other nonmetallic impurities in the target material can affect the deposited film and can lead to defective or imperfect devices.

Conventional analysis of metallic materials such as PVD target materials for impurities such as oxides typically involves dissolution techniques where a small sample of material is dissolved in acid. The resulting solution is filtered to retain un-dissolved particles on the filter. The size and number of particles retained on the filter is then determined to ascertain the amount of impurity particles present in the metallic material. However, this conventional technique presents a number of problems. First, the particles agglomerate during the filtering process giving inaccurate size and number data. Second, the imaging system used to measure particles is limited to detecting particles having a size greater than about 2 microns. Third, the process is relatively labor and time intensive. Accordingly, it is desirable to develop alternative techniques for metallic material analysis.

SUMMARY OF THE INVENTION

In one aspect the invention encompasses a method of detecting impurities in a metal-containing article. An article comprising a metal material to be analyzed is provided. A portion of the metal material is removed and is solubilized in an acid-comprising liquid to produce a liquid sample. The liquid sample is subjected to an incident laser beam and light scattered from the sample is detected.

In one aspect the invention encompasses a method of analyzing a physical vapor deposition target material. A portion of the target material is removed from the target and is rinsed with an acid-comprising solution. A sample is prepared for analysis by dissolving metal comprised by the portion of material. The sample is subjected to an incident laser beam and the scatter of the laser beam is detected to determine the number of particles present in the sample within a particular size range.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with one aspect of the present invention, novel methodology is presented which can be utilized for analysis of metallic materials. Methodology of the invention can be extremely useful for determining material quality, especially for high purity metal materials where impurities and/or particle defects in the material can determine the usefulness of a material or suitability of the material for a particular purpose.

One area of particular interest for application of methodology of the invention is for determining and/or quantifying impurities and/or particle defects in physical vapor deposition target material. The methodology can be utilized to determine material suitability prior to final fabrication steps in formation of the target, or can be utilized after target formation either prior to any sputtering event or after a portion of the target material has been removed by sputtering processes. The methodology of the invention can also be useful for analysis of physical vapor deposited films and layers. In particular instances, both the target material and the resulting film can be analyzed to determine if particles or impurities present in the deposited layer are a result of the presence of particles or impurities in the target or if additional or other factors are contributing to contaminants present in the resulting film.

Although the methodology of the invention is described with respect to analyzing target material and deposited films, it is to be understood that the methodology can be adapted for analyzing alternative metals and alloy materials. Accordingly, the invention contemplates performing the described methodology on alternate metal articles and especially those metal articles where the presence of particles and contaminants can affect the article's suitability for an intended purpose.

Figure 1:
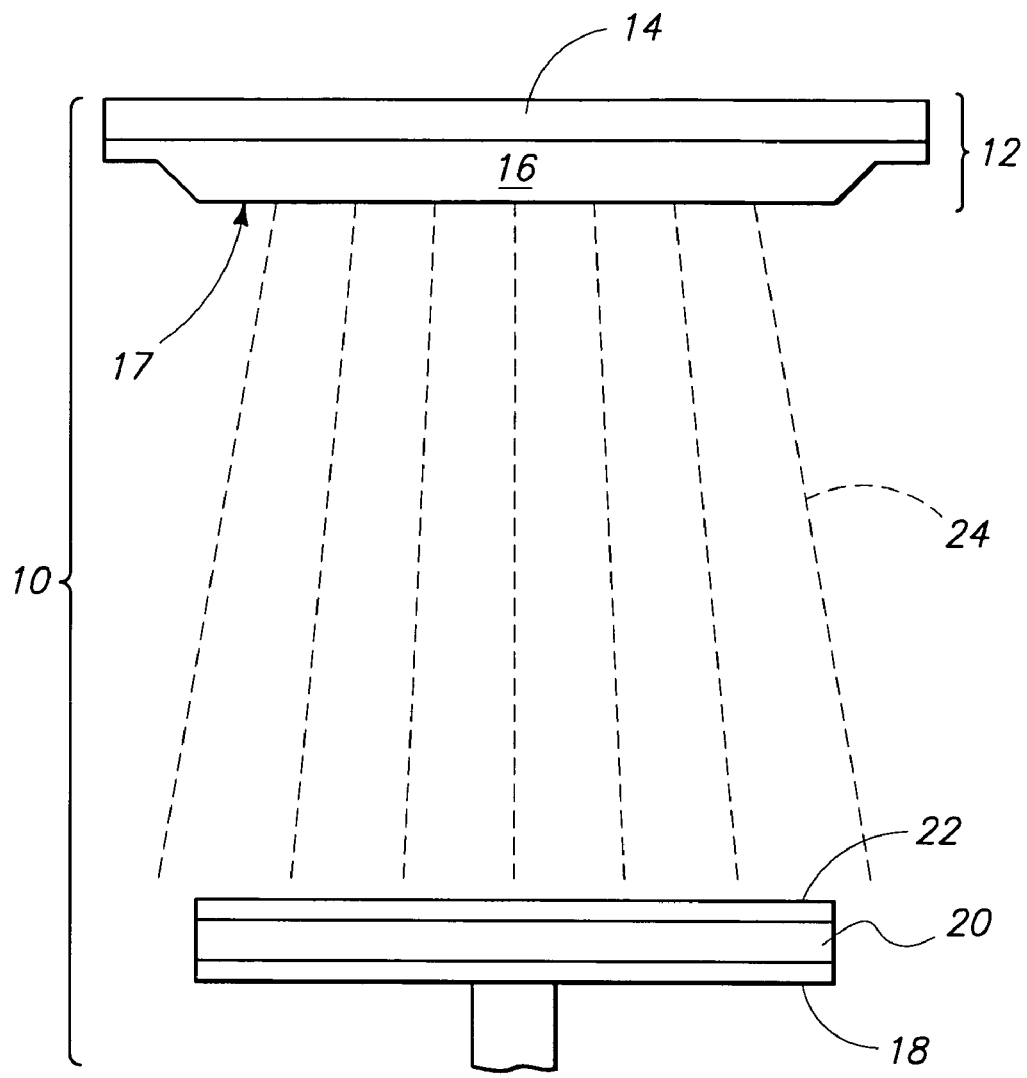
FIG. 1 is a diagrammatic view of a portion of an exemplary physical vapor deposition apparatus.
Figure 2:
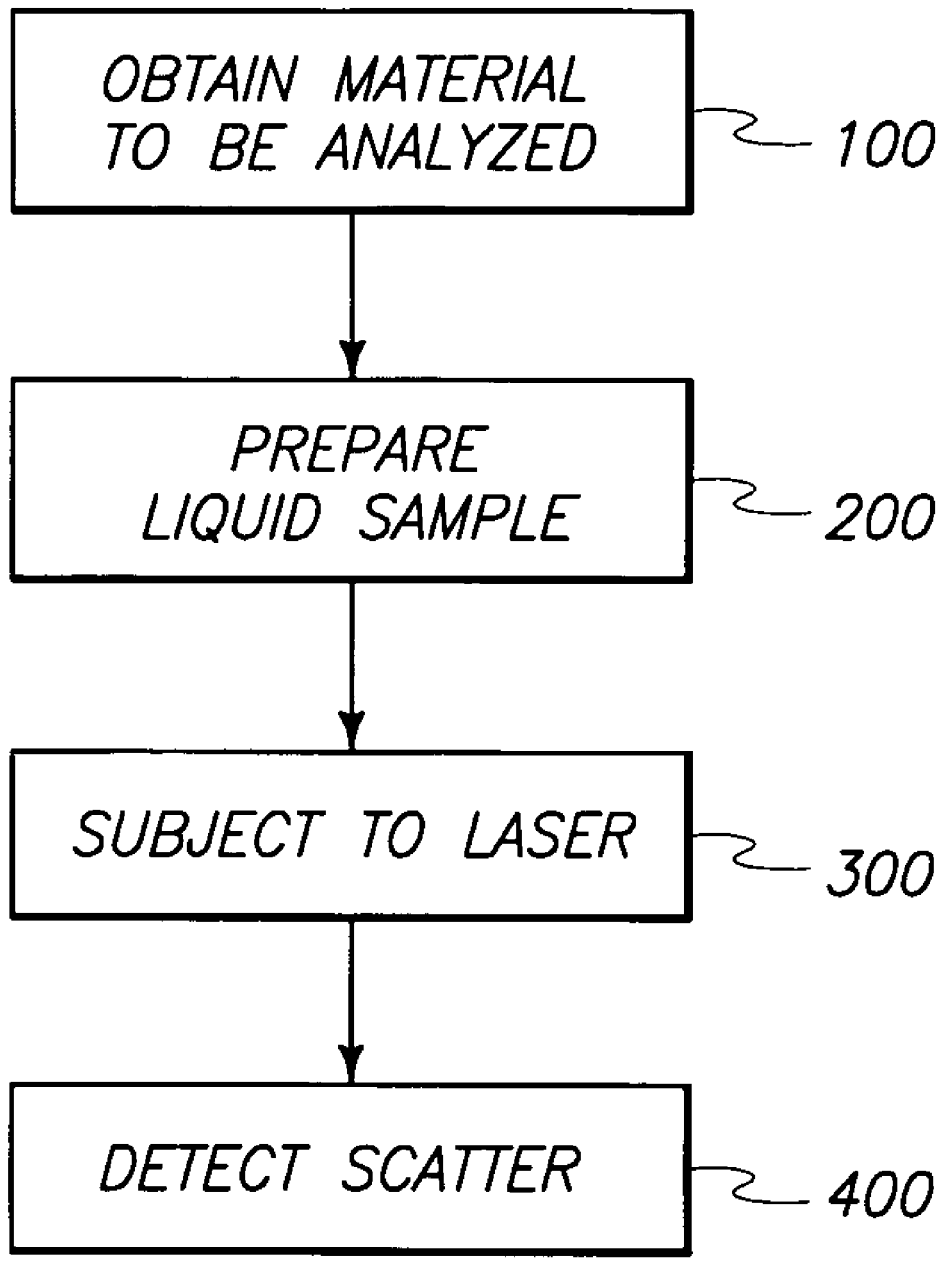
FIG. 2 is a flowchart diagram outlining methodology in accordance with one aspect of the invention.

Methodology in accordance with the invention is described generally with reference to FIG. 2. In an initial process 100 material to be analyzed is obtained by, for example, cutting or otherwise removing a portion of the physical vapor deposition target or other metallic article to be analyzed. The removed portion can then preferably be washed or rinsed to remove any surface contaminants prior to analysis. An exemplary rinse solution can be, for example, an acid or base solution in which the target material is at least slightly soluble.

For performing methodology of the invention all reagents and analysis solutions are preferably prepared utilizing high purity or ultra pure materials and are additionally filtered prior to contacting the material to be analyzed.

The size of the portion of material utilized is not limited to a particular amount and can be, for example, from about 10 to about 30 grams. Preferably, the sample mass is sufficiently large to constitute a sample representative of the article. It is to be understood that the invention contemplates utilizing smaller samples where the available material is limited, such as where a deposited material is to be analyzed.

As illustrated in FIG. 2, the portion of material to be analyzed is utilized to prepare a liquid sample in a subsequent process 200. For purposes of the present description, the term "liquid sample" can refer to a sample containing a liquid, including but not limited to a liquid solution, and which may contain particles and/or undissolved material. Typically, a liquid sample will consist essentially of or consist of a solution and contaminant particles contributed by the dissolved metal material.

Preparation of the liquid sample involves dissolving of the metal material into an appropriate solvent. Appropriate solvents which can be utilized are acid solutions having sufficient quantity and strength to dissolve the metal material. Alternative appropriate solvents are base solutions having sufficient quantity and strength to dissolve the metal material. As will be understood by those skilled in the art, the strength and particular acid or base utilized can be determined based upon the metal(s) or alloy of the target material. Exemplary target materials which can be analyzed utilizing methodology in accordance with the invention can be metal materials or alloys containing metals including but not limited to, Cu, Al, Ti, Ta, Ru, W, Au, Ag, Mo, Co, Ni, Se, Te, Ge, Sn, Pb, and mixtures and alloys thereof. Accordingly, an appropriate acid, acid mixture, base or base mixture, can be chosen to dissolve the particular material to be analyzed.

In contrast with conventional dissolution techniques, the prepared liquid sample of the invention is analyzed without filtering after dissolution of the metal. By avoiding filtering, agglomeration of particles during filtering is avoided. Accordingly, fewer inaccuracies are encountered during the particle counting.

As illustrated in FIG. 2, the prepared liquid sample can be subjected to a laser beam in process 300. Process 300 can be performed utilizing a laser counting apparatus. Alternatively, process 300 can utilize a broad band beam emitted from a non-coherent, broad band light source counting apparatus. Although the methodology of the invention is described below with respect to laser analysis, it is to be understood that the methodology applies also to utilizing a broad band light source.

When the sample is subjected to an incident laser beam, particles within the sample cause scattering of the beam. Accordingly, a scatter detection step 400 can be performed to provide information about the particle count and size of particles present within the liquid sample.

Process steps 300 and 400 are preferably performed utilizing a liquid particle counter comprising a laser source and optical detector or detector array. Conventional use of liquid laser particles counters has typically been limited to water analysis, and in some instances liquid chemical reagent/solvent purity analysis. However, the present study reveals that methodology of the invention can be practiced utilizing an appropriately sensitive commercially available liquid particle counter, and can accurately analyze contaminant particle content in a liquid containing a dissolved metal sample. An exemplary commercially available particle counter which can be utilized is a LIQUILAZ® counter (Particle Measuring Systems, Inc. Boulder Colo.).

When analyzing liquid samples prepared from physical vapor deposition target materials, particles present in the liquid sample will typically comprise oxides or other nonmetallic particles/inclusions which were present in the target material prior to dissolution. For purposes of the present description, the term inclusion refers to any inorganic compound present in the metal/alloy which is not a component of the metal/alloy, including but not limited to graphite, carbides and sulfates. Typically these particles will consist of particles of a particle size (particle diameter) of less than about 20 microns. Accordingly, an appropriate liquid laser analysis system for purposes of the invention will have sensitivity sufficient to detect and count particles having a particle size of less than 20 microns.

The wavelength of the incident laser beam is not limited to a particular value. An appropriate laser wavelength can be determined based upon the particular particle size range to be analyzed/counted.

The particular wavelength chosen for the incident beam can preferably be such that the incident beam is minimally or negligibly deflected or scattered by the solution of the liquid sample. Accordingly, scatter of the beam can be substantially due to particles within the liquid sample.

A detector array can be provided to perform scatter detection process 400. Based upon the scatter pattern obtained, particle size can be determined.

Where a range of particle sizes is present in the liquid sample, the sample can be subjected to a first laser wavelength and, after detection of the scattered pattern resulting from the first laser, the liquid sample can be subjected to a second laser beam having a wavelength that differs from the first laser beam. Additional rounds of laser analysis using differing wavelengths can be performed to maximize particle size information. Since liquid laser analysis sensitivity is dependent upon wavelength, small particles (as small as 0.2 micron) can be detected utilizing short wavelengths.

In particular instances, high purity target materials will contain only particles/inclusions having very small (less than or equal to 5 microns) particle size. In particular instances the particles will consist of particles of a size less than about one micron. Methodology of the invention can be utilized to accurately determine the number of particles and particle size for nonmetallic particles/inclusions present in even extreme high purity PVD targets. In particular instances, the size can be determined to a resolution of about 1 nm. Accordingly, methodology of the invention can detect and analyze particles much smaller than previous technologies allowed. Additionally, the processing of the invention is less labor intensive than the dissolution/filtering techniques conventionally utilized.

Figure 3:
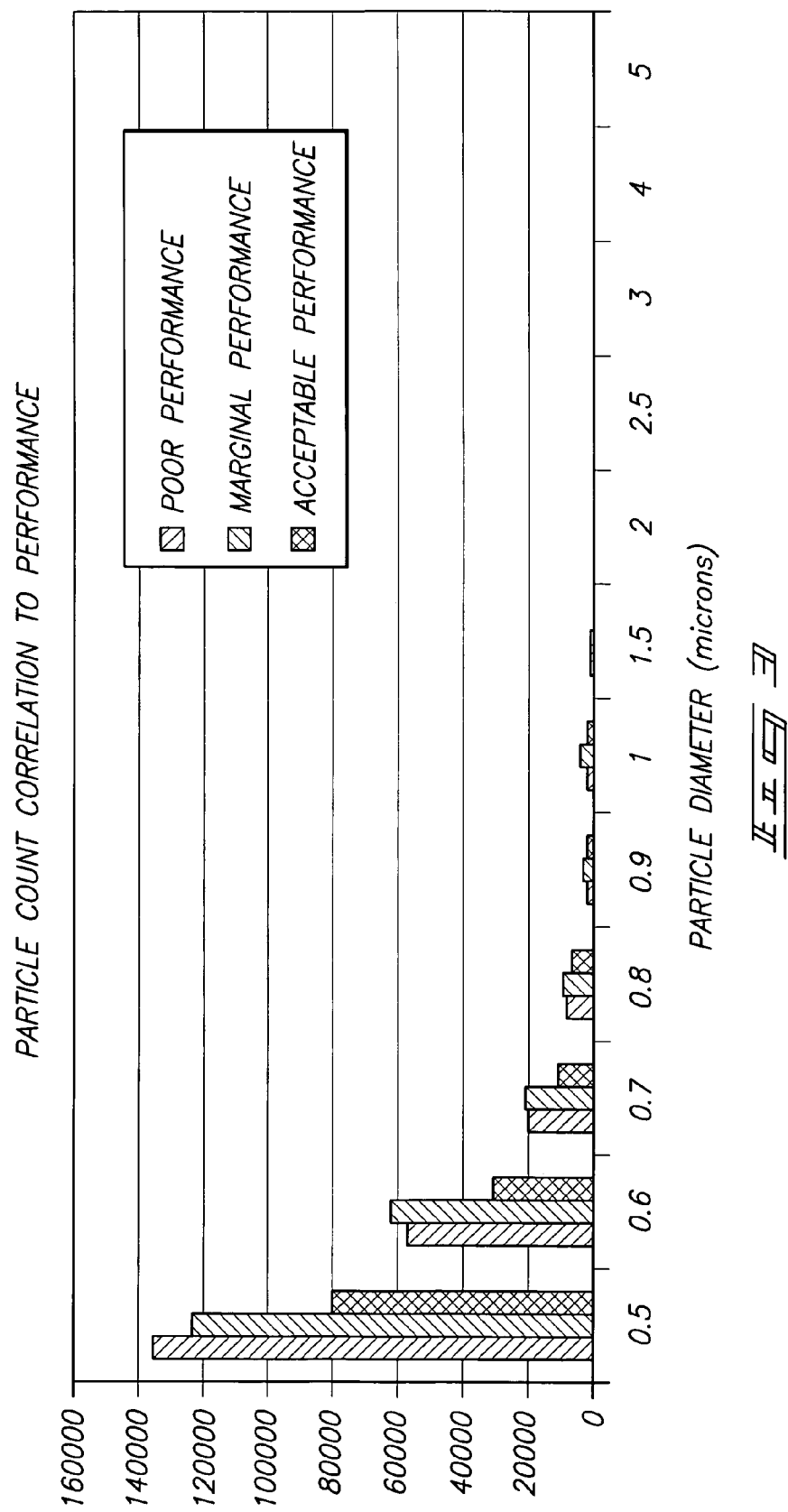
FIG. 3 shows the particle count correlation to sputtering target performance as determined by methodology in accordance with the present invention.

Referring to FIG. 3, such illustrates the particle count correlation to sputtering target performance. Data presented in FIG. 3 were obtained from three copper alloy sputtering targets utilizing a CLS700 liquid sampler coupled to a LIQUI-LAZ® SO2 particle counter. As shown, the particle count information obtained utilizing methodology of the invention correlates well with the observed suitability of particular targets for semiconductor fabrication. These results indicate that analysis of target material in accordance with the invention can determine contaminant particle/inclusions content which can predict or indicate target suitability. Analysis in accordance with the invention can be utilized to analyze target material during target fabrication or prior to use of the target. The methodology can additionally be utilized for target and/or film analysis to troubleshoot a sputtering system where deposited films or device constructions are contaminated or flawed. Such information can indicate whether all or a portion of a particular target contains contaminants, particles and/or inclusions, or whether contaminants or flaws are being introduced from other sources or influences.

In addition to analyzing physical vapor deposition target material and deposited fill material, methodology of the present invention can be especially useful for applications such as analyzing metal materials such as IMP coils and anode materials.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of detecting impurities in a metal-containing article, comprising: providing an article comprising a metal material;
    solubilizing a portion of metal material in a liquid to produce a liquid sample containing undissolved impurities, the liquid being one of an acid solution or a base solution;
    subjecting the liquid sample to at least one of an incident laser beam and a non-coherent broad band beam; and
    detecting light scattered from the original impurities in the liquid sample; and
    counting the number of particles present in the liquid sample.

2. The method of claim 1 wherein the impurities present in the metal material comprise at least one of non-metallic particles and inclusions present in the metal material.

3. The method of claim 1 wherein the impurities present in the metal material consist essentially of the at least one of non-metallic particles and inclusions.

4. The method of claim 1 wherein impurities present in the liquid sample comprise particles in the size range of less than 100 μm.

5. The method of claim 1 wherein impurities present in the liquid sample comprise particles, wherein all particles in the sample have a particle size of less than about 1 μm.

6. The method of claim 1 wherein the detecting scattered light comprises obtaining a scatter pattern, and further comprising determining particle sizes of particulate impurities present in the liquid sample based upon the scatter pattern.

7. The method of claim 6 wherein the determined particle sizes are less than 100 μm.

8. The method of claim 6 wherein the determined particle sizes are less than 20 μm diameter.

9. The method of claim 6 wherein the determined particle sizes are less than 1 μm.

10. The method of claim 6 wherein the determined particle sizes are less than 0.5 μm.

11. The method of claim 1 wherein the metal-containing article is a sputtering target.

12. The method of claim 11 wherein the portion of the metal material is removed prior to any sputtering from the target.

13. The method of claim 11 wherein the portion of the metal material is removed after sputtering from the target has occurred.

14. The method of claim 1 wherein the metal-containing article comprises a layer of the metal material deposited by sputtering from a sputtering target.

15. The method of claim 1 wherein the incident laser beam is a first laser beam having a first wavelength, and further comprising after subjecting the liquid sample to the first incident laser beam, subjecting the liquid sample to a second incident laser beam having a second wavelength that differs from the first wavelength.

16. The method of claim 15 wherein scatter from the first laser beam provides particle size and count information for a first set of particles within a first size range, and wherein scatter from the second laser beam provides particle size and count information for a second set of particles within a second size range.

17. A method of analyzing a physical vapor deposition target material comprising:
    rinsing a portion of material with an acid-comprising solution;
    preparing a sample for analysis by dissolving metal comprised by the portion of material in a liquid;
    subjecting the liquid sample to an incident beam selected from a laser beam and a non-coherent broad band beam;
    detecting scatter of the incident beam to determine the number of particles present in the liquid sample within a particle size range.

18. The method of claim 17 wherein the particles present in the sample comprise at least one of non-metallic compounds and inclusions.

19. The method of claim 17 wherein the particle size range is less than 20 μm.

20. The method of claim 17 wherein the target material comprises at least one metal selected from the group consisting of Al, Cu, Ti, Ta, Ru, W, Au, Ag, Mo, Co, Ni, Se, Ni, Se, Te, Ge, Sn and Pb.

* * * * *